United States Patent
Somekh et al.

(10) Patent No.: US 11,166,723 B2
(45) Date of Patent: Nov. 9, 2021

(54) SURGICAL HANDLE ASSEMBLY MODES OF OPERATION

(71) Applicant: Lexington Medical, Inc., Billerica, MA (US)

(72) Inventors: Gonen Somekh, Kerem Maharal (IL); Shani Mann, Needham, MA (US); Leon Amariglio, Lexington, MA (US)

(73) Assignee: Lexington Medical, Inc., Billerica, MA (US)

(*) Notice: Subject to any disclaimer, the term of this patent is extended or adjusted under 35 U.S.C. 154(b) by 297 days.

(21) Appl. No.: 16/577,097

(22) Filed: Sep. 20, 2019

(65) Prior Publication Data

US 2020/0093486 A1    Mar. 26, 2020

Related U.S. Application Data

(60) Provisional application No. 62/734,488, filed on Sep. 21, 2018.

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/072* (2013.01);
(Continued)

(58) Field of Classification Search
CPC ............ A61B 17/072; A61B 17/07207; A61B 17/115; A61B 17/068; A61B 17/0686; A61B 2017/07214; A61B 2017/07257; A61B 2017/07271; A61B 2017/2927; A61B 2017/2943; A61B 2017/00407
(Continued)

(56) References Cited

U.S. PATENT DOCUMENTS 4,978,049 A   12/1990   Green
5,300,081 A   4/1994   Young et al.
(Continued)

FOREIGN PATENT DOCUMENTS

CN   1985768   6/2007
CN   101194853   6/2008
(Continued)

OTHER PUBLICATIONS

International Searching Authority., International Search Report and Written Opinion dated Jun. 18, 2018 for PCT Application No. PCT/US2018/025988 Filed Apr. 4, 2018, 9 pages.
(Continued)

*Primary Examiner* — Scott A Smith
(74) *Attorney, Agent, or Firm* — Brooks, Cameron & Huebsch, PLLC (57) ABSTRACT

The present disclosure includes apparatuses for a surgical handle assembly. An example apparatus includes a toothed rack, a tab configured to provide a reverse mode of operation for the toothed rack by engaging a reverse gear, and a trigger gear connected to the reverse gear and to a movable handle member configured to reverse the toothed rack linearly in a proximal direction in response to actuation of the movable handle member.

20 Claims, 8 Drawing Sheets

(51) Int. Cl.
*A61B 17/29* (2006.01)
*A61B 17/00* (2006.01)

(52) U.S. Cl.
CPC .............. *A61B 2017/00407* (2013.01); *A61B 2017/07214* (2013.01); *A61B 2017/07257* (2013.01); *A61B 2017/07271* (2013.01); *A61B 2017/2943* (2013.01)

(58) Field of Classification Search
USPC .............. 227/19, 175.1, 175.2, 176.1, 180.1; 606/1, 139, 219
See application file for complete search history.

(56) References Cited

U.S. PATENT DOCUMENTS

| | | | |
|---|---|---|---|
| 5,326,013 | A | 7/1994 | Green et al. |
| RE34,680 | E | 8/1994 | Lieser |
| 5,484,095 | A * | 1/1996 | Green ................ A61B 17/0686 227/175.1 |
| 5,489,292 | A | 2/1996 | Tovey et al. |
| 5,507,426 | A | 4/1996 | Young et al. |
| 5,762,256 | A | 6/1998 | Mastri et al. |
| 5,865,361 | A | 2/1999 | Milliman et al. |
| 5,901,895 | A | 5/1999 | Heaton et al. |
| 6,109,500 | A | 8/2000 | Alli et al. |
| 6,905,057 | B2 * | 6/2005 | Swayze ............ A61B 17/07207 227/176.1 |
| 7,044,353 | B2 | 5/2006 | Mastri et al. |
| 7,097,089 | B2 | 8/2006 | Marczyk |
| 7,128,254 | B2 * | 10/2006 | Shelton, IV ..... A61B 17/07207 227/181.1 |
| 7,225,963 | B2 | 6/2007 | Scirica |
| 7,225,964 | B2 * | 6/2007 | Mastri ................ A61B 17/0684 227/176.1 |
| 7,246,734 | B2 * | 7/2007 | Shelton, IV ..... A61B 17/07207 227/175.1 |
| 7,624,902 | B2 | 12/2009 | Marczyk et al. |
| 7,753,245 | B2 * | 7/2010 | Boudreaux ...... A61B 17/07207 227/175.1 |
| 7,794,475 | B2 * | 9/2010 | Hess ................... A61B 17/105 606/219 |
| 7,832,408 | B2 | 11/2010 | Shelton, IV et al. |
| 7,837,079 | B2 | 11/2010 | Holsten et al. |
| 7,845,535 | B2 | 12/2010 | Scircia |
| 7,922,063 | B2 * | 4/2011 | Zemlok ................ A61B 17/068 227/176.1 |
| 7,963,431 | B2 | 6/2011 | Scirica |
| 7,967,178 | B2 | 6/2011 | Scirica et al. |
| 8,056,789 | B1 | 11/2011 | White et al. |
| 8,328,822 | B2 | 12/2012 | Huitema et al. |
| 8,336,751 | B2 | 12/2012 | Scirica |
| 8,342,378 | B2 | 1/2013 | Marczyk et al. |
| 8,424,736 | B2 | 4/2013 | Scirica et al. |
| 8,608,043 | B2 | 12/2013 | Scirica |
| 8,684,247 | B2 | 4/2014 | Scirica et al. |
| 8,695,865 | B2 | 4/2014 | Smith et al. |
| 9,364,218 | B2 | 6/2016 | Scirica |
| 9,393,016 | B2 | 7/2016 | Scirica et al. |
| 9,861,358 | B2 | 1/2018 | Marczyk et al. |
| 10,383,634 | B2 | 8/2019 | Shelton, IV |
| 2005/0116009 | A1 | 6/2005 | Milliman |
| 2006/0079912 | A1 | 4/2006 | Whitfield et al. |
| 2007/0262116 | A1 | 11/2007 | Hueil et al. |
| 2008/0017693 | A1 | 1/2008 | Mastri et al. |
| 2008/0083810 | A1 | 4/2008 | Marczyk |
| 2008/0179374 | A1 | 7/2008 | Beardsley et al. |
| 2009/0062614 | A1 | 3/2009 | Adzich et al. |
| 2009/0145947 | A1 | 6/2009 | Scirica |
| 2010/0001036 | A1 | 1/2010 | Marczyk et al. |
| 2010/0264193 | A1 | 10/2010 | Huang et al. |
| 2011/0290854 | A1 | 12/2011 | Timm et al. |
| 2012/0286019 | A1 | 11/2012 | Hueil |
| 2013/0092719 | A1 | 4/2013 | Kostrzewski |
| 2013/0304115 | A1 | 11/2013 | Miyamoto |
| 2014/0224856 | A1 | 8/2014 | Smith et al. |
| 2015/0342605 | A1 | 12/2015 | Abbott et al. |
| 2015/0374396 | A1 | 12/2015 | Strobl et al. |
| 2016/0058441 | A1 | 3/2016 | Morgan et al. |
| 2017/0172577 | A1 | 6/2017 | Wenchell et al. |
| 2017/0281177 | A1 | 10/2017 | Harris et al. |
| 2018/0168599 | A1 | 6/2018 | Bakos et al. |
| 2018/0289370 | A1 | 10/2018 | Amariglio et al. |
| 2018/0368832 | A1 | 12/2018 | Marecki et al. |

FOREIGN PATENT DOCUMENTS

| | | |
|---|---|---|
| CN | 101965156 | 2/2011 |
| EP | 1021130 | 7/2000 |
| EP | 1908410 | 4/2008 |
| EP | 2586382 | 9/2013 |
| EP | 2777530 | 9/2014 |
| EP | 2886020 | 6/2015 |
| EP | 2886071 | 6/2015 |
| WO | 2016/107586 | 7/2016 |

OTHER PUBLICATIONS

International Searching Authority., International Search Report and Written Opinion dated Oct. 22, 2018 for PCT Application No. PCT/US2018/038909 Filed Jun. 22, 2018, 10 pages.

International Searching Authority., International Search Report and Written Opinion dated Oct. 4, 2019 for PCT Application No. PCT/US2019/040315 Filed Jul. 2, 2019, 9 pages.

CN First Office Action dated Feb. 28, 2020 for CN Application No. 201880022626.9 Filed Sep. 27, 2019, 14 pages.

International Search Report and Written Opinion dated Apr. 7, 2020 for PCT Application No. PCT/US2020/013694 filed Jan. 15, 2020, 8 pages.

* cited by examiner

SURGICAL HANDLE ASSEMBLY MODES OF OPERATION

PRIORITY INFORMATION

This application claims benefit of U.S. Provisional Application No. 62/734,488 filed Sep. 21, 2018, the specification of which is incorporated herein by reference.

TECHNICAL FIELD

The present disclosure relates generally to a surgical handle assembly, and more particularly, to modes of operation for a surgical handle assembly.

BACKGROUND

A surgical handle assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. For example, a row of staples can have a linear length between 30 mm and 60 mm. A staple can be ejected by actuation of a movable handle member that is a part of the surgical handle assembly of the surgical stapler.

DETAILED DESCRIPTION

The present disclosure includes apparatuses for a surgical handle assembly. An example apparatus includes a toothed rack, a tab configured to provide a reverse mode of operation for the toothed rack by engaging a reverse gear, and a trigger gear connected to the reverse gear and to a movable handle member configured to reverse the toothed rack linearly in a proximal direction in response to actuation of the movable handle member.

In a number of embodiments, the mode selection capability can be a button and/or a tab. The surgical handle assembly is described with the button and tab example throughout the present disclosure for ease of understanding and illustration; however, embodiments are not limited to a button and a tab. While a button and tab are shown by example, one or more buttons and/or one or more tabs can be in the embodiments disclosed herein. In this example, the button when pressed and/or set to a particular position can provide a forward mode of operation for the toothed rack. The tab when pressed and/or set to a particular position can provide a reverse mode of operation for the toothed rack. Use of the surgical handle assembly with a surgical stapler in the forward mode of operation can advance the toothed rack in the distal direction and when coupled to a reloadable cartridge can deploy a first number of staples. Use of the surgical handle assembly with a surgical stapler in the reverse mode of operation can reverse a toothed rack in a proximal direction. In a number of embodiments, the forward mode of operation or the reverse mode of operation can be selected based on deploying or reloading staples, for example.

In a number of embodiments, the surgical handle assembly can include a toothed rack, a tab, and a trigger gear. The toothed rack can include an upper toothed rack and a lower toothed rack. The tab can be configured to provide a reverse mode of operation for the toothed rack by engaging a reverse gear. The trigger gear can be connected to the reverse gear and to a movable handle member. The trigger gear can be configured to reverse the toothed rack linearly in a proximal direction in response to actuation of the movable handle member.

In a number of embodiments, the reverse gear is engaged via a ratchet coupled to the trigger gear via a ratchet shaft. The ratchet can be biased by a ratchet spring to engage the reverse gear. The reverse gear can contact a reverse direction gear to reverse the toothed rack linearly in the proximal direction.

The trigger gear can include a slot. A timing latch can be coupled to the slot of the trigger gear. The timing latch can prevent a ratchet from engaging the reverse gear until the movable handle member reaches a home position.

The tab can be coupled to a lever drag and the lever drag can be coupled to a latch. The tab can move a lever drag in a counterclockwise direction to advance a latch in a distal direction to prevent the latch from contacting the ratchet.

The tab can also be coupled to a reverse rack tab, which can be coupled to a driving pawl. In the forward mode of operation, the reverse rack tab allows the driving pawl to contact a lower toothed rack and advance the toothed rack in a linearly distal direction when the movable handle member is actuated by the user.

In the reverse mode of operation, the reverse rack tab prevents the driving pawl from contacting a lower toothed rack to allow the toothed rack to move in a linearly proximal direction. In the reverse mode of operation, the reverse gear contacts the upper toothed rack to move the toothed rack in a linearly proximal direction when the movable handle member is actuated by the user.

In a number of embodiments, the surgical handle assembly can include a toothed rack, a button, and a driving pawl. The button can provide a forward mode of operation for the toothed rack by contacting a ratchet to disengage a reverse gear.

The driving pawl can be connected to a movable handle member. The driving pawl can be configured to advance the toothed rack linearly in a distal direction in response to actuation of the movable handle member. The tab can prevent the toothed rack from advancing by disengaging the driving pawl in the reverse mode of operation. The driving pawl can be disengaged in response to a user pressing the tab. The tab, when pressed can actuate the reverse rack tab, which actuates the driving pawl to disengage from the lower toothed rack.

The button can lower the swing pivot to allow the latch to move in the proximal direction and contact the ratchet. The latch can prevent the ratchet from engaging the reverse gear. The latch can be biased in the proximal direction, by a spring, for example.

Once the button is pushed, a lever drag keeps the button in a pressed position. One or more staples can be ejected from the surgical stapling apparatus in response to the button being pressed a second time and the movable handle member being actuated.

In a number of embodiments, transition from the forward mode of operation to the reverse mode of operation can be accomplished by a user pressing the tab. The tab may be pressed in order to reverse the toothed rack linearly in a proximal direction when actuating the movable handle member. Transition from the reverse mode of operation to the forward mode of operation can be accomplished by pressing the button. Here, the button may be pressed in order to advance the toothed rack linearly in a distal direction when actuating the movable handle member.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "X", "Y", "N", "M", etc., particularly with respect to reference numerals in the drawings, indicate that a number of the particular feature so designated can be included. It is also to be understood that the terminology used herein is for the purpose of describing particular embodiments only, and is not intended to be limiting. As used herein, the singular forms "a", "an", and "the" can include both singular and plural referents, unless the context clearly dictates otherwise. In addition, "a number of", "at least one", and "one or more" (e.g., a number of pivot points) can refer to one or more pivot points, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 216 may reference element "16" in FIG. 2A, and a similar element may be referenced as 316 in FIG. 3. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

Figure 1A:
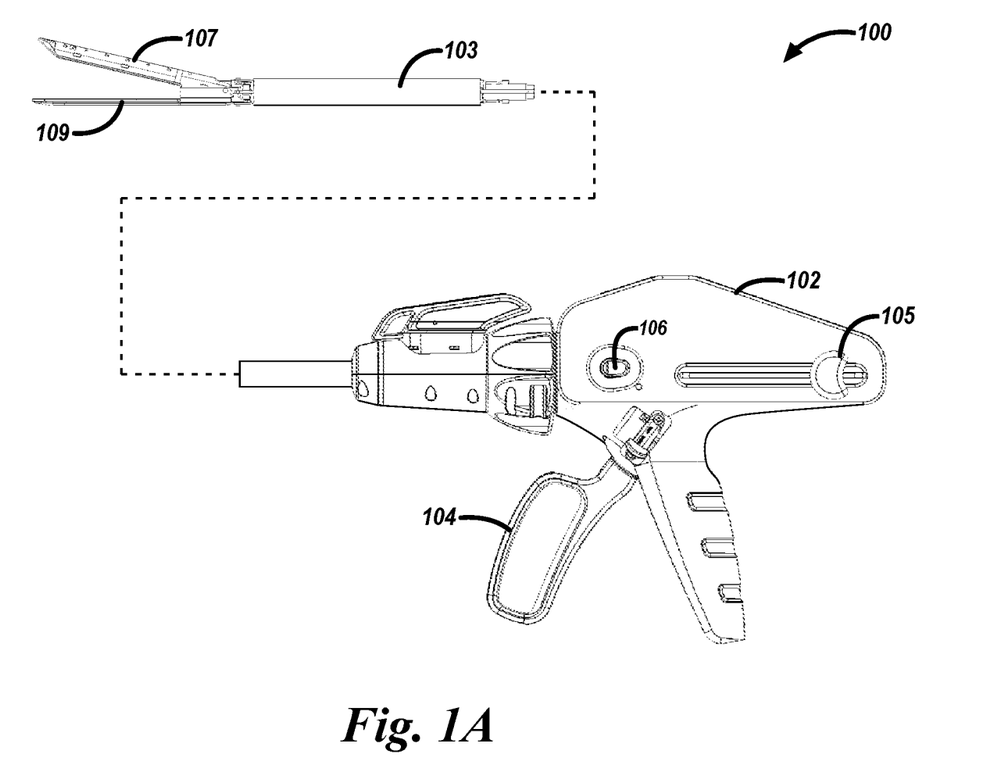
FIG. 1A is a schematic diagram of a surgical stapling apparatus including a surgical handle assembly in accordance with a number of embodiments of the present disclosure.

FIG. 1A is a schematic diagram of a surgical stapling apparatus 100 including a surgical handle assembly 102 in accordance with a number of embodiments of the present disclosure. In the example, a surgical stapler apparatus 100 can include a surgical handle assembly 102 and a reloadable cartridge assembly 103.

As shown in the example of FIG. 1A, the reloadable cartridge assembly 103, e.g. a disposable loading unit, can be releasably secured to a distal end of an elongated body of the surgical handle assembly 102. In this example, the reloadable cartridge assembly 103 can include a first elongated member 107 and a second elongated member 109 that can be used to clamp tissue. One of the elongated members can house one or more staple cartridges. The other elongated member can have an anvil that can be used to form a staple when driven from the staple cartridge. As mentioned, a surgical stapling apparatus 100 can receive reloadable cartridge assemblies having rows of staples. In a number of embodiments, third party reloadable cartridge and/or reloadable cartridge assemblies may be used with the surgical handle assembly 102 and embodiments of surgical handle assembly 102 may be configured to receive the same.

Figure 1B:
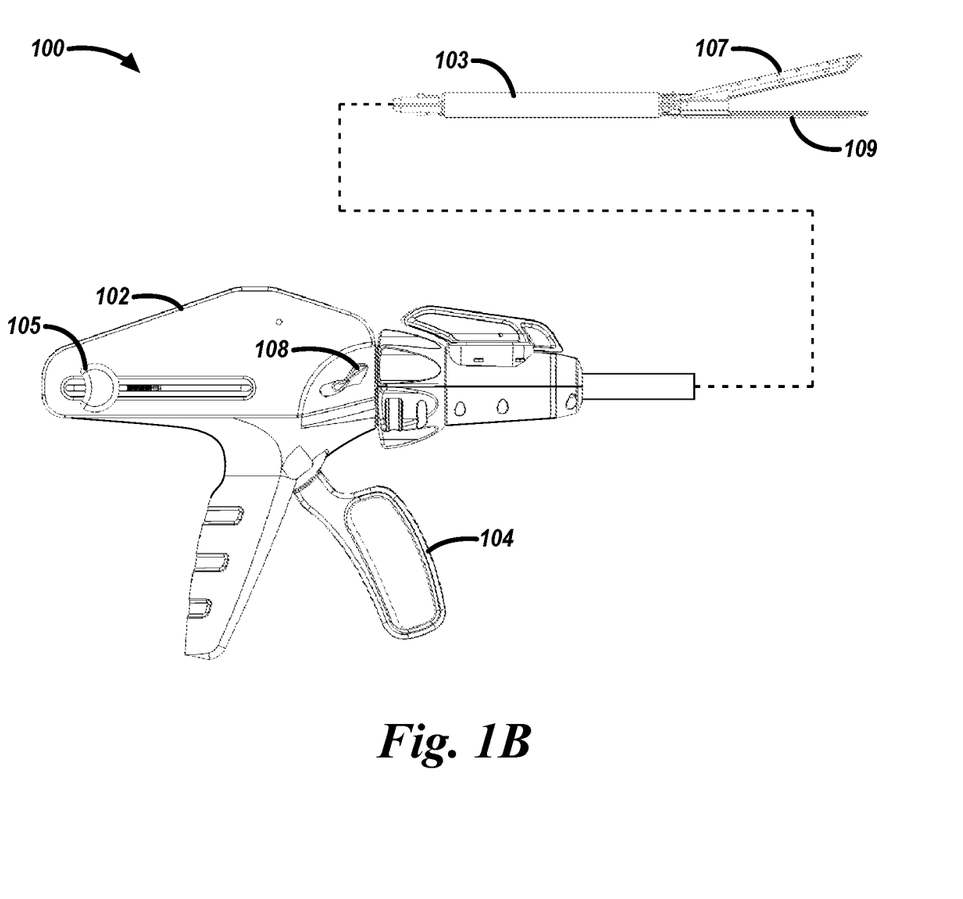
FIG. 1B is a schematic diagram of a surgical stapling apparatus including a surgical handle assembly in accordance with a number of embodiments of the present disclosure.
Figure 4A:
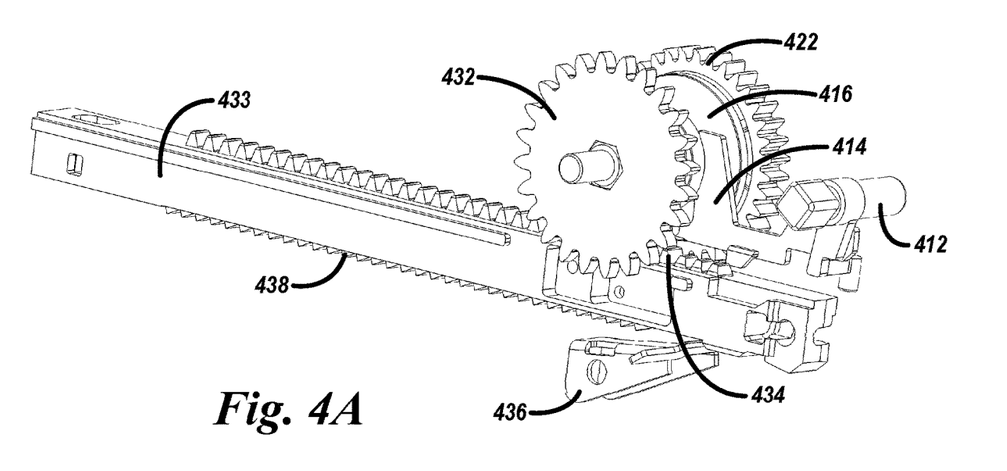
FIG. 4A is a schematic diagram of a surgical handle assembly including a driving pawl, a toothed rack, a lever drag, a latch, a trigger gear, a ratchet, and a reverse gear in a forward mode of operation in accordance with a number of embodiments of the present disclosure.

A staple can be ejected by actuation of a movable handle member 104 that is a part of a surgical handle assembly 102 to the surgical stapling apparatus 100. Actuation of the movable handle member 104 can actuate a toothed rack (e.g., toothed rack 433 in FIG. 4) to eject a number of staples. For example, in a forward mode of operation, actuation of the movable handle member 104 may clamp tissue via the first elongated member 107 and the second elongated member 109 and/or eject a number of staples by actuating the toothed rack in the distal direction. The surgical handle assembly 102 can be in a forward mode of operation when a button 106 of the surgical handle assembly 102 is set to a particular position. FIG. 1B is a schematic diagram of a surgical stapling apparatus 100 including a surgical handle assembly 102 in accordance with a number of embodiments of the present disclosure. In the example, a surgical stapler apparatus 100 can include a surgical handle assembly 102 and a reloadable cartridge assembly 103.

As shown in the example of FIG. 1B, the reloadable cartridge assembly 103, e.g. a disposable loading unit, can be releasably secured to a distal end of an elongated body of the surgical handle assembly 102. In this example, the reloadable cartridge assembly 103 can include a first elongated member 107 and a second elongated member 109 that can be used to clamp tissue.

Actuation of the movable handle member 104 can actuate a toothed rack (e.g., toothed rack 433 in FIG. 4). For example, in a reverse mode of operation, actuation of the movable handle member 104 may unclamp the tissue from the first elongated member 107 and the second elongated member 109 and/or reverse the toothed rack in a proximal direction. The surgical handle assembly 102 can be in a reverse mode of operation when a tab 108 of the surgical handle assembly 102 is set to a particular position. The surgical handle assembly 102 is described with the surgical stapling apparatus 103 example throughout the present disclosure for ease of understanding and illustration. However, embodiments are not limited to use with a surgical stapling apparatus 100.

In a number of embodiments, the surgical handle assembly 102 can include retract grips 105. The retract grips 105 can be used to unclamp the tissue from the first elongated member 107 and the second elongated member 109 and/or reverse the toothed rack (e.g., toothed rack 433 in FIG. 4) in a proximal direction by a user pulling the retract grips 105 in a proximal direction. In some examples, the retract grips 105 can be used in response to the surgical stapling apparatus 100 failing to operate in a reverse mode of operation.

Figure 2A:
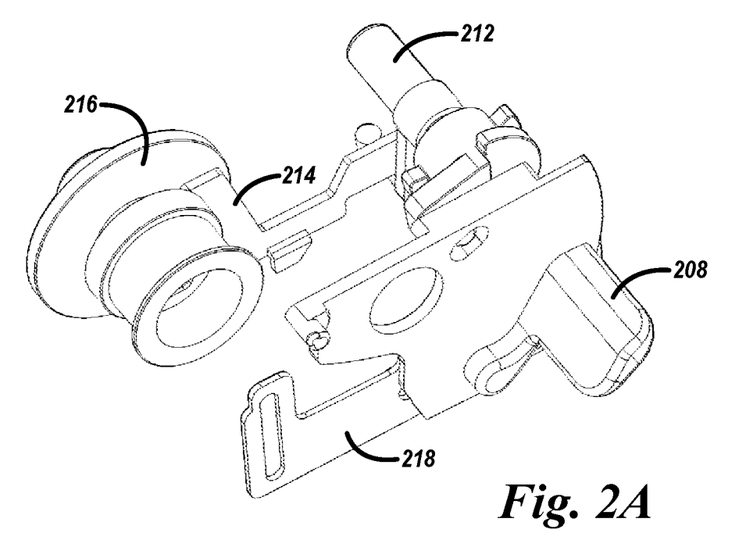
FIG. 2A is a schematic diagram of a surgical handle assembly including a tab, a reverse rack tab, a lever drag, a latch, and a ratchet in a forward mode of operation in accordance with a number of embodiments of the present disclosure.

FIG. 2A is a schematic diagram of a surgical handle assembly including a tab 208, a reverse rack tab 218, a lever drag 212, a latch 214, and a ratchet 216 in a forward mode of operation in accordance with a number of embodiments of the present disclosure.

The tab 208 can be configured to provide a reverse mode of operation. The tab 208 can be coupled to the lever drag 212 and the lever drag 212 can be coupled to the latch 214. The latch 214 can contact the ratchet 216 in a forward mode of operation. In the forward mode of operation, the latch 214 can prevent the ratchet 216 from engaging a reverse gear (e.g., reverse gear 322 in FIG. 3). The latch 214 can be biased in the proximal direction, by a spring, for example so that the latch 214 is biased to contact the ratchet 216. The tab 208 can also be biased by a spring. The tab 208 can be biased in the forward mode of operation, but the ratchet 216 can prevent the tab 208 from going into the forward mode of operation.

The tab 208 can also be coupled to a reverse rack tab 218, which is coupled to the driving pawl (e.g., driving pawl 436 in FIG. 4). In the forward operation mode, the reverse rack tab allows the driving pawl to contact a lower toothed rack (e.g., lower toothed rack 438 in FIG. 4) and advance the lower toothed rack in a linearly distal direction when the movable handle member (e.g., movable handle member 104 in FIG. 1A) is actuated by the user.

In a number of embodiments, transition from the forward mode of operation to the reverse mode of operation can be accomplished by a user pressing the tab 208. The tab 208 may be pressed in order to reverse the toothed rack (e.g., toothed rack 433 in FIG. 4) linearly in a proximal direction when actuating the movable handle member (e.g., movable handle member 104 in FIG. 1A). Here, the movable handle member may be actuated in order to advance the toothed rack linearly in a distal direction.

Figure 2B:
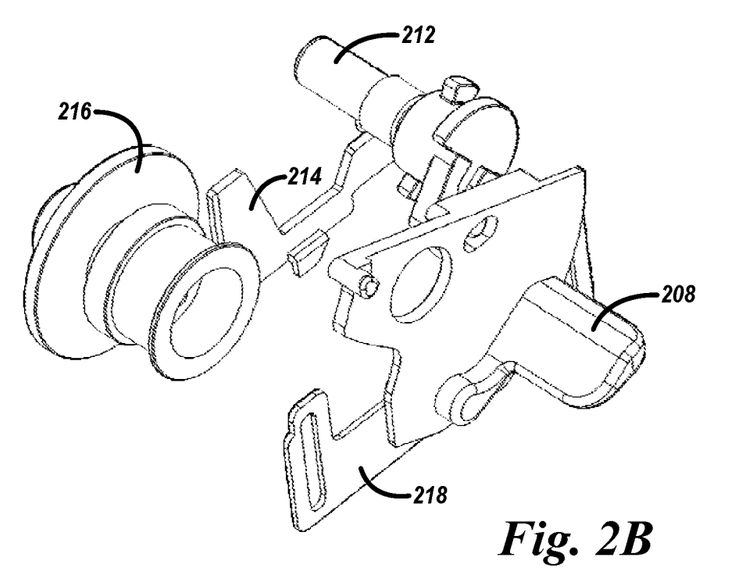
FIG. 2B is a schematic diagram of a surgical handle assembly including a tab, a reverse rack tab, a lever drag, a latch, and a ratchet in a reverse mode of operation in accordance with a number of embodiments of the present disclosure.

FIG. 2B is a schematic diagram of a surgical handle assembly including a tab 208, a reverse rack tab 218, a lever drag 212, a latch 214, and a ratchet 216 in a reverse mode of operation in accordance with a number of embodiments of the present disclosure.

The tab 208 can be configured to provide a reverse mode of operation. The tab 208 can be coupled to a lever drag 212 and the lever drag 212 can be coupled to a latch 214. The latch 214 can be biased in the proximal direction, by a spring, for example. The tab 208 can cause the lever drag 212 to rotate to advance the latch 214 in a distal direction to prevent the latch 214 from contacting a ratchet 216.

The tab 208 can also be coupled to a reverse rack tab 218, which is coupled to a driving pawl (e.g., driving pawl 436 in FIG. 4). In the reverse mode of operation, the reverse rack tab 218 prevents the driving pawl from contacting the lower toothed rack 438 to allow the toothed rack (e.g., toothed rack 433 in FIG. 4) to move in a linearly proximal direction when the movable handle member (e.g., movable handle member 104 in FIG. 1B) is actuated by the user.

In a number of embodiments, transition from the forward mode of operation to the reverse mode of operation can be accomplished by a user pressing the tab 208. The tab 208 may be pressed in order to reverse the toothed rack (e.g., toothed rack 433 in FIG. 4) linearly in a proximal direction when actuating the movable handle member (e.g., movable handle member 104 in FIG. 1A).

Figure 3:
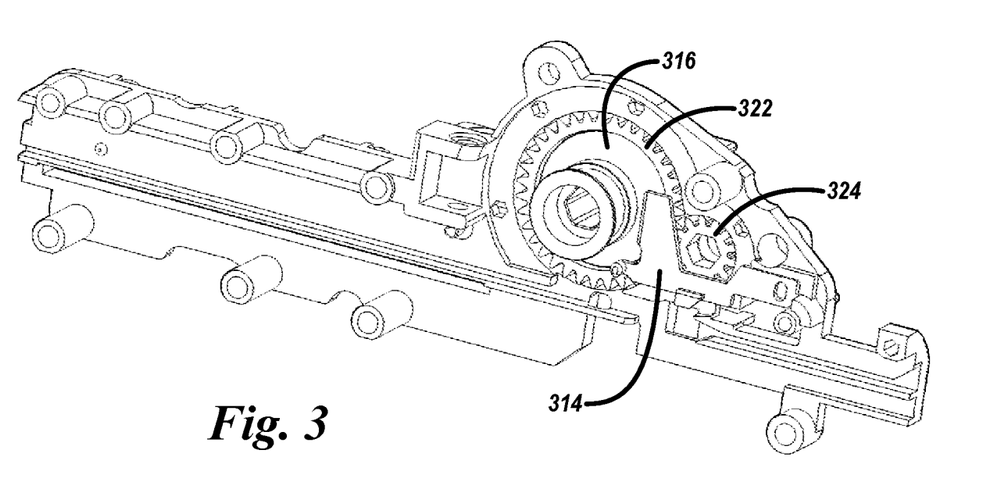
FIG. 3 is a schematic diagram of a surgical handle assembly including a latch, a reverse direction gear, a reverse gear, and a ratchet in accordance with a number of embodiments of the present disclosure.

FIG. 3 is a schematic diagram of a surgical handle assembly including a latch 314, a reverse direction gear 324, a reverse gear 322, and a ratchet 316 in accordance with a number of embodiments of the present disclosure.

Figure 6A:
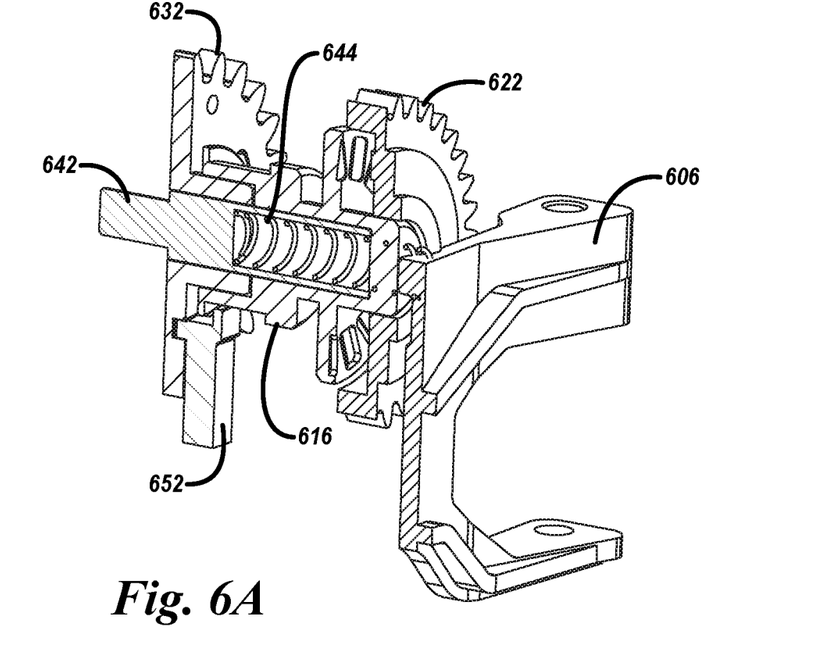
FIG. 6A is a schematic diagram of a surgical handle assembly including a timing latch, a ratchet spring, a ratchet shaft, a ratchet, a trigger gear, a reverse gear, and a button in a forward mode of operation in accordance with a number of embodiments of the present disclosure.

In this example, the surgical handle assembly (e.g., surgical handle assembly 100 in FIG. 1B) is in a reverse mode of operation. In the reverse mode of operation, the latch 314 is biased away from the ratchet 316 so that the latch 314 does not contact the ratchet 316 and/or does not prevent the ratchet 316 from moving. The ratchet 316 can also be biased toward the reverse gear 322 by a ratchet spring (e.g., ratchet spring 644 in FIG. 6), for example. Since the latch 314 is not contacting the ratchet 316 and/or not preventing the ratchet 316 from moving in a reverse mode of operation, ratchet 316 can engage the reverse gear 322. When the ratchet 316 is engaged with the reverse gear 322, the reverse gear 322 will rotate in response to the user actuating the movable handle member (e.g., movable handle member 104 in FIG. 1B).

In a number of embodiments, the reverse gear 322 can contact a reverse direction gear 324. The reverse direction gear 324 can be used to change the direction of rotation, so that the surgical handle assembly, in the reverse mode of operation, will reverse the toothed rack (e.g., toothed rack 433 in FIG. 4) linearly in a proximal direction in response to actuation of the movable handle member.

In a number of embodiments, the surgical handle assembly can be in a forward mode of operation. In the forward mode of operation, the latch 314 is contacting the ratchet 316. Since the latch 314 is contacting the ratchet 316, the ratchet 316 cannot engage the reverse gear 322 and the reverse gear 322 will not rotate in response to the user actuating the movable handle member (e.g., movable handle member 104 in FIG. 1A).

FIG. 4A is a schematic diagram of a surgical handle assembly including a driving pawl 436, a toothed rack 433, a lever drag 412, a latch 414, a trigger gear 432, a ratchet 416, and a reverse gear 422 in a forward mode of operation in accordance with a number of embodiments of the present disclosure. In some examples, the toothed rack 433 can include an upper toothed rack 434 and a lower toothed rack 438.

In this example, the surgical handle assembly (e.g., surgical handle assembly 100 in FIG. 1A) is in a forward mode of operation. In the forward mode of operation, the lever drag 412 moves and/or permits the latch 414 to move in a linearly proximal direction to allow the latch 414 to contact the ratchet 416. The latch 414 in contact with the ratchet 416 prevents the ratchet 416 from engaging the reverse gear 422. When the ratchet 416 is not engaged to the reverse gear 422, the trigger gear 432 can be rotated in response to the user actuating the movable handle member (e.g., movable handle member 104 in FIG. 1A) without also rotating the reverse gear 422.

In the forward mode of operation, the driving pawl 436 can contact the lower toothed rack 438 when the movable handle member (e.g., movable handle member 104 in FIG. 1A) is actuated by the user. The driving pawl 436 can advance the toothed rack 433 in a linearly distal direction.

Figure 4B:
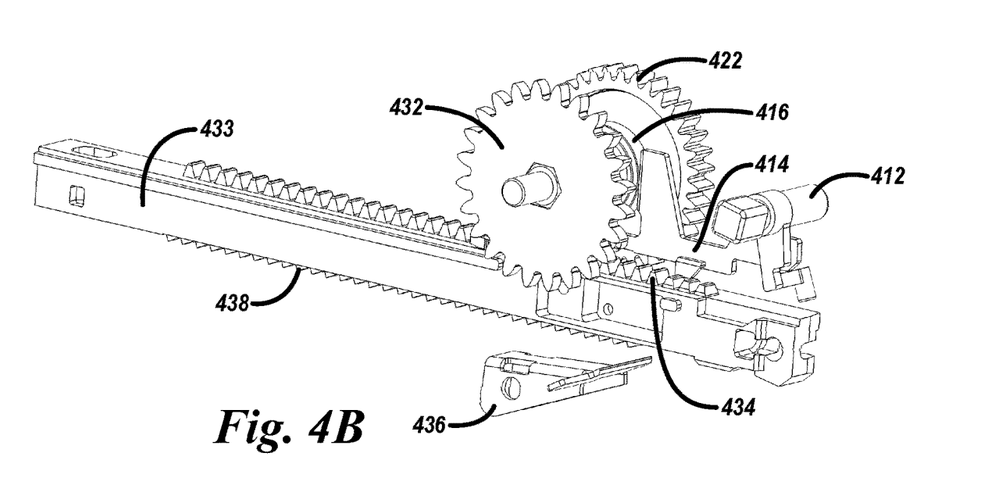
FIG. 4B is a schematic diagram of a surgical handle assembly including a driving pawl, a toothed rack, a lever drag, a latch, a trigger gear, a ratchet, and a reverse gear in a reverse mode of operation in accordance with a number of embodiments of the present disclosure.

FIG. 4B is a schematic diagram of a surgical handle assembly including a driving pawl 436, a toothed rack 433, a lever drag 412, a latch 414, a trigger gear 432, a ratchet 416, and a reverse gear 422 in a reverse mode of operation in accordance with a number of embodiments of the present disclosure. In some examples, the toothed rack 433 can include an upper toothed rack 434 and a lower toothed rack 438.

In this example, the surgical handle assembly (e.g., surgical handle assembly 102 in FIG. 1B) is in a reverse mode of operation. In the reverse mode of operation, the lever drag 412 moves the latch 414 in a linearly distal direction to prevent the latch 414 from contacting the ratchet 416. The latch 414 not in contact with the ratchet 416 allows the ratchet 416 to engage the reverse gear 422. When the ratchet 416 is engaged with the reverse gear 422, the trigger gear 432 and the reverse gear 422 can be rotated in response to the user actuating the movable handle member (e.g., movable handle member 104 in FIG. 1B).

In the reverse mode of operation, the driving pawl 436 can be disengaged. The driving pawl 436 can be disengaged to prevent the driving pawl 436 from contacting the lower toothed rack 438 when the movable handle member (e.g., movable handle member 104 in FIG. 1B) is actuated by the user. The driving pawl 436 can be disengaged in response to a user pressing the tab (e.g., tab 208 in FIG. 2). The tab, when pressed can actuate the reverse rack tab (e.g., reverse rack tab 218 in FIG. 2), which actuates the driving pawl 436 to disengage from the lower toothed rack 438.

Figure 5:
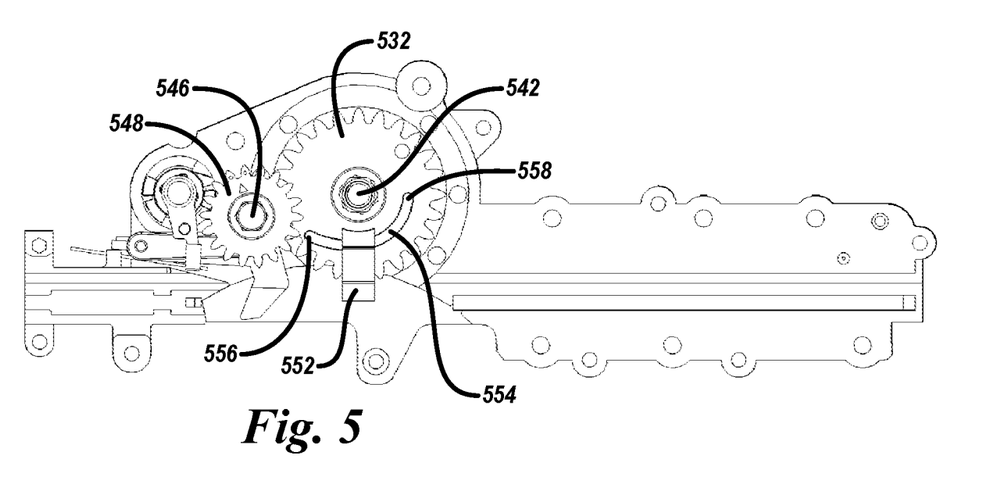
FIG. 5 is a schematic diagram of a surgical handle assembly including a timing latch, a trigger gear, a ratchet shaft, a rack pinion, and a rack pinion shaft in accordance with a number of embodiments of the present disclosure.

FIG. 5 is a schematic diagram of a surgical handle assembly including a timing latch 552, a trigger gear 532, a ratchet shaft 542, a rack pinion 548, and a rack pinion shaft 546 in accordance with a number of embodiments of the present disclosure.

The trigger gear 532 can include a slot 554. The timing latch 552 can be coupled to the slot 554 of the trigger gear 532. When the timing latch 552 is located at a first end 556 of the slot 554, the movable handle member (e.g., movable handle member 104 in FIG. 1A) can be at a home position. The movable handle member can be at a home position when the movable handle member is not being actuated by the user. For example, the movable handle member is not being actuated by the user when the movable handle member is in the farthest linearly distal position the movable handle member can travel.

The timing latch 552 can allow the ratchet (e.g., ratchet 416 in FIG. 4) to engage the reverse gear (e.g., reverse gear 422 in FIG. 4) in response to the movable handle member reaching the home position. In some examples, the timing latch 552 does not contact the ratchet when the movable handle member is in the home position allowing the ratchet to move along the ratchet shaft 542 toward the reverse gear. The ratchet can be biased towards the reverse gear so that the ratchet will move toward the ratchet if it is not being held away from the reverse gear by the timing latch 552.

When the timing latch 552 is located at a second end 558 of the slot 554, the movable handle member (e.g., movable handle member 104 in FIG. 1A) can be at an index position. The movable handle member can be at an index position when the movable handle member is fully actuated by the user. For example, the movable handle member can be fully actuated by the user squeezing the movable handle member in a linearly proximal direction until the movable handle member cannot travel any further in the linearly proximal direction.

The timing latch 552 can prevent the ratchet (e.g., ratchet 416 in FIG. 4) from engaging the reverse gear (e.g., reverse gear 422 in FIG. 4) when the movable handle member (e.g., movable handle member 104 in FIG. 1A) is not in the home position. For example, the timing latch 552 can prevent the ratchet from engaging the reverse gear when the movable handle member is in an index position and/or when the movable handle member is between the home position and the index position. In some examples, the timing latch 552 contacts the ratchet when the movable handle member is in the index position and between the index position and the home position preventing the ratchet from moving along the ratchet shaft 542 toward the reverse gear.

In a number of embodiments, a reverse direction gear (e.g., reverse direction gear 324 in FIG. 3) can be coupled to the rack pinion shaft 546. The rack pinion gear 548 can also be coupled to the rack pinion shaft 546. In a reverse mode of operation, the reverse gear (e.g., reverse gear 422 in FIG. 4) can rotate and contact the reverse direction gear to rotate the reverse direction gear in the opposite direction of the reverse gear. Since the rack pinion gear 548 is on the same rack pinion shaft 546 as the reverse direction gear, the rack pinion gear 548 will rotate in the same direction as the reverse direction gear. When the rack pinion gear 548 is rotated, the rack pinion gear 548 can rotate and contact the upper toothed rack (e.g., upper toothed rack 434 in FIG. 4) and move the toothed rack (e.g., toothed rack 433 in FIG. 4) in a linearly proximal direction.

FIG. 6A is a schematic diagram of a surgical handle assembly including a timing latch 652, a ratchet spring 644, a ratchet shaft 642, a ratchet 616, a trigger gear 632, a reverse gear 622, and a button 606 in a forward mode of operation in accordance with a number of embodiments of the present disclosure. FIG. 6A includes a cross-sectional isometric view of a portion of a surgical handle assembly.

As described above in FIG. 5, the trigger gear 632 can include a slot (e.g., slot 554 in FIG. 5) and the timing latch 652 can be coupled to the slot. The ratchet 616 can be biased toward the reverse gear 622 by the ratchet spring 644. The timing latch 652 can prevent the ratchet 616 from engaging the reverse gear 622 when the movable handle member (e.g., movable handle member 104 in FIG. 1A) is not in the home position. For example, the timing latch 652 can prevent the ratchet 616 from engaging the reverse gear 622 when the movable handle member is in an index position and/or when the movable handle member is between the home position and the index position. In some examples, the timing latch 652 contacts the ratchet 616 when the movable handle member is in the index position and between the index position and the home position. The timing latch 652 contacting the ratchet 616 prevents the ratchet 616 from moving along the ratchet shaft 642 toward the reverse gear 622 until the movable handle member reaches the home position.

In a number of embodiments, the user can put the surgical handle assembly (e.g., surgical handle assembly 102 in FIG. 1A) in a forward mode of operation by pressing the button 606. When pressed, the button 606 can contact the ratchet 616, overcome the bias of the ratchet spring 644, and disengage the ratchet 616 from the reverse gear 622.

Figure 6B:
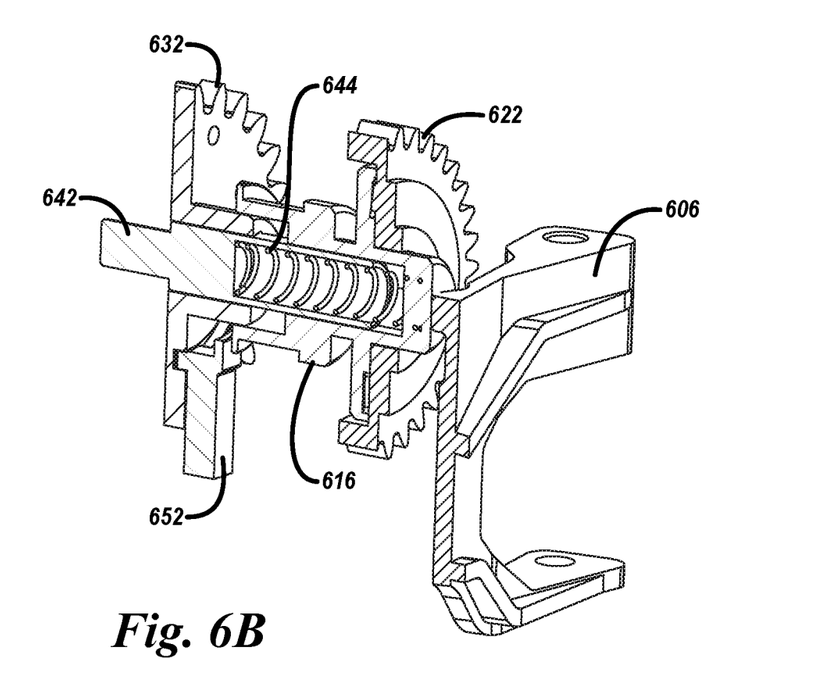
FIG. 6B is a schematic diagram of a surgical handle assembly including a timing latch, a ratchet spring, a ratchet shaft, a ratchet, a trigger gear, a reverse gear, and a button in a reverse mode of operation in accordance with a number of embodiments of the present disclosure.

FIG. 6B is a schematic diagram of a surgical handle assembly including a timing latch 652, a ratchet spring 644, a ratchet shaft 642, a ratchet 616, a trigger gear 632, a reverse gear 622, and a button 642 in a reverse mode of operation in accordance with a number of embodiments of the present disclosure. FIG. 6B includes a cross-sectional isometric view of a portion of a surgical handle assembly.

As described above in FIG. 5, the trigger gear 632 can include a slot (e.g., slot 554 in FIG. 5) and the timing latch 652 can be coupled to the slot. The timing latch 652 can allow the ratchet 616 to engage the reverse gear 622 in response to the movable handle member (e.g., movable handle member 104 in FIG. 1B) reaching the home position. In some examples, the timing latch 652 does not contact the ratchet 616 when the movable handle member is in the home position, allowing the ratchet 616 to move along the ratchet shaft 642 toward the reverse gear 622. The ratchet 616 can be biased towards the reverse gear 622 by a ratchet spring 644. The ratchet 616 can be biased so that the ratchet 616 will move toward the reverse gear 622 if it is not being held away from the reverse gear 622 by the timing latch 652.

In a number of embodiments, the user can put the surgical handle assembly (e.g., surgical handle assembly 102 in FIG. 1B) in a reverse mode of operation by pressing the tab (e.g., tab 108 in FIG. 1B). When the surgical handle assembly is in a reverse mode of operation, the button 606 does not contact the ratchet 616 and/or the contact does not overcome the bias of the ratchet spring 644. As such, the button 606 in the reverse mode of operation allows the ratchet 616 to engage the reverse gear 622.

Figure 7A:
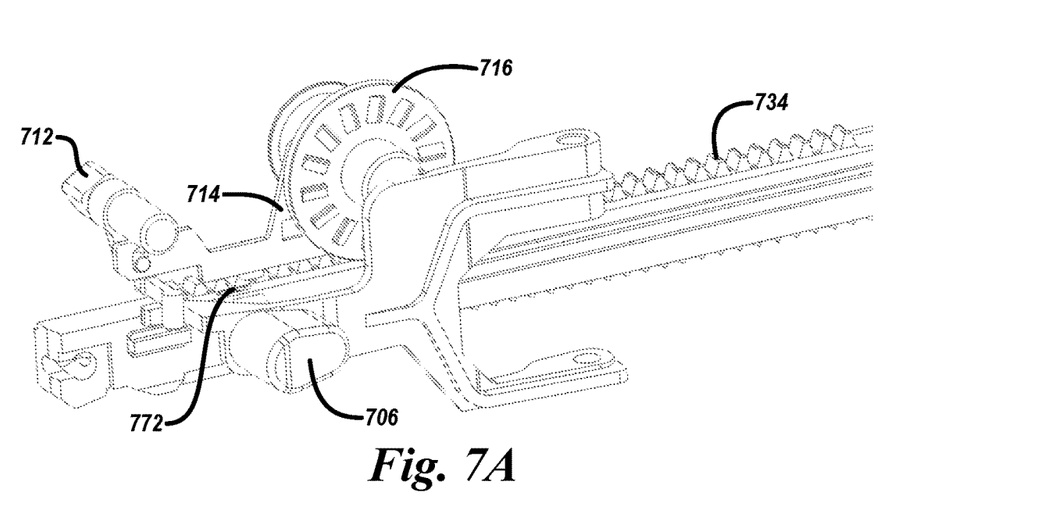
FIG. 7A is a schematic diagram of a surgical handle assembly including a swing pivot, an upper toothed rack, a button, a ratchet, and a latch in a forward mode of operation in accordance with a number of embodiments of the present disclosure.

FIG. 7A is a schematic diagram of a surgical handle assembly including a swing pivot 772, an upper toothed rack 734, a ratchet 716, a lever drag 712, a button 706, and a latch 714 in a forward mode of operation in accordance with a number of embodiments of the present disclosure.

In a number of embodiments, the swing pivot 772 can be coupled to the button 706. The swing pivot 772 can be lowered beneath the upper toothed rack 734 in response to the user pressing the button to put the surgical handle assembly (e.g., surgical handle assembly 102 in FIG. 1A) into a forward mode of operation.

In a forward mode of operation, the swing pivot 772 is lowered to prevent the swing pivot 772 from contacting the latch 714. The latch 714 can be biased toward the ratchet (e.g., ratchet 616 in FIG. 6) by a spring, for example. When the swing pivot 772 is lowered by the button, the latch 714 can move linearly in the proximal direction to contact the ratchet and prevent the ratchet from engaging the reverse gear (e.g., reverse gear 622 in FIG. 6).

Once the user presses the button 706, the lever drag 712 maintains the button 706 in a pressed position to prevent the handle assembly (e.g., handle assembly 102 in FIG. 1A) from switching from the forward mode of operation to the reverse mode of operation.

In the forward mode of operation, the reloadable cartridge assembly (e.g., reloadable cartridge assembly 103 in FIG. 1) can clamp tissue via the first elongated member (e.g., first elongated member 107 in FIG. 1) moving toward the second elongated member (e.g., second elongated member 109 in FIG. 1) in response to the movable handle member (e.g., movable handle member 104 in FIG. 1) being actuated from the home position to the index position.

Once the reloadable cartridge assembly (e.g., reloadable cartridge assembly 103 in FIG. 1) is in the clamped position, the user can either press the button 706 or actuate the movable handle member (e.g., movable handle member 104 in FIG. 1). The surgical handle assembly switches to a reverse mode of operation and the reloadable cartridge assembly unclamps the tissue in response to the user actuating the movable handle member. For example, as the movable handle member returns to the home position from the index position, the first elongated member (e.g., first elongated member 107 in FIG. 1) and the second elongated member (e.g., second elongated member 109 in FIG. 1) can move away from each other unclamping the tissue.

The surgical handle assembly stays in the forward mode of operation and the reloadable cartridge assembly ejects a number of staples in response to the user pressing the button 706 and actuating the movable handle member (e.g., movable handle member 104 in FIG. 1). For example, the first elongated member (e.g., first elongated member 107 in FIG. 1) and the second elongated member (e.g., second elongated member 109 in FIG. 1) will not move away from each other in response to the movable handle member returning to the home position. As the user moves the movable handle member, the toothed rack 734 will continue to move in a distal direction causing the number of staples to be ejected.

Figure 7B:
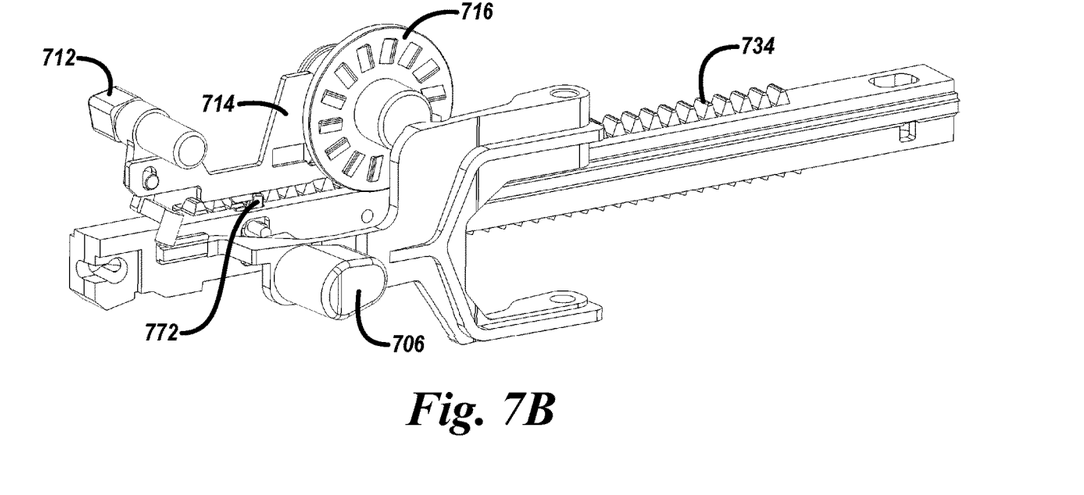
FIG. 7B is a schematic diagram of a surgical handle assembly including a swing pivot, an upper toothed rack, a button, a ratchet, and a latch in a reverse mode of operation in accordance with a number of embodiments of the present disclosure.

FIG. 7B is a schematic diagram of a surgical handle assembly including a swing pivot 772, an upper toothed rack 734, a ratchet 716, a lever drag 712, a button 706, and a latch 714 in a reverse mode of operation in accordance with a number of embodiments of the present disclosure.

In a number of embodiments, the swing pivot 772 is biased above the toothed rack 734 surface by a spring. In response to the user pressing the movable handle member (e.g., movable handle member 104 in FIG. 1A) in a forward mode of operation, the swing pivot 772 can be coupled to the latch 714, which is coupled to the lever drag 712 and the tab (e.g., tab 108 in FIG. 1B). When the latch 714 is coupled to the swing pivot 772, the latch 714 can move in a distal direction and cannot contact the ratchet (e.g., ratchet 616 in FIG. 6) to prevent it from engaging the reverse gear (e.g., reverse gear 622 in FIG. 6). When latch 714 is not in contact with the ratchet (e.g., ratchet 616 in FIG. 6), the reverse gear and the ratchet can engage to place the surgical handle assembly (e.g., surgical handle assembly 102 in FIG. 1) into a reverse mode of operation.

In the reverse mode of operation, when the user actuates the movable handle member (e.g., movable handle member 104 in FIG. 1), the toothed rack 734 can move in a proximal direction until it is in the most proximal position. In some examples, when the toothed rack 734 is in the most proximal position, the first elongated member (e.g., first elongated member 107 in FIG. 1) and the second elongated member (e.g., second elongated member 109 in FIG. 1) can move away from each other unclamping the tissue.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A surgical handle assembly apparatus, comprising:
a toothed rack;
a tab configured to:
provide a reverse mode of operation for the toothed rack by engaging a reverse gear; and
a trigger gear connected to the reverse gear and to a movable handle member configured to:
reverse the toothed rack linearly in a proximal direction in response to actuation of the movable handle member.

2. The apparatus of claim 1, wherein the reverse gear is engaged via a ratchet coupled to the trigger gear via a ratchet shaft.

3. The apparatus of claim 2, wherein the ratchet is biased toward the reverse gear by a ratchet spring.

4. The apparatus of claim 1, wherein the tab is further configured to cause a lever drag to rotate.

5. The apparatus of claim 4, wherein the lever drag advances a latch in a distal direction to prevent the latch from contacting a ratchet.

6. The apparatus of claim 1, wherein the reverse gear contacts a reverse direction gear to reverse the toothed rack linearly in the proximal direction.

7. A surgical handle assembly apparatus, comprising:
a toothed rack;
a tab configured to:
prevent the toothed rack from advancing in a linearly distal direction by disengaging a driving pawl via a reverse rack tab connected to the tab and the driving pawl; and
a trigger gear connected to a reverse gear and a movable handle member configured to:
reverse the toothed rack linearly in a proximal direction in response to actuation of the movable handle member.

8. The apparatus of claim 7, wherein the trigger gear includes a slot.

9. The apparatus of claim 8, wherein a timing latch is coupled to the slot of the trigger gear.

10. The apparatus of claim 9, wherein the timing latch can prevent a ratchet from engaging the reverse gear until the movable handle member reaches a home position.

11. The apparatus of claim 7, wherein the tab is coupled to a lever drag.

12. The apparatus of claim 11, wherein a latch is coupled to the lever drag.

13. A surgical handle assembly apparatus, comprising:
a toothed rack;
a button configured to:
provide a forward mode of operation for the toothed rack by contacting a ratchet to disengage the ratchet from a reverse gear; and
a driving pawl connected to a movable handle member configured to:
advance the toothed rack linearly in a distal direction in response to actuation of the movable handle member.

14. The apparatus of claim 13, wherein the button is further configured to move a latch in a proximal direction to allow the latch to contact the ratchet.

15. The apparatus of claim 13, wherein a latch prevents the ratchet from engaging the reverse gear.

16. The apparatus of claim 15, wherein the latch is biased in the proximal direction.

17. The apparatus of claim 13, wherein the button is further configured to move a lever drag.

18. The apparatus of claim 17, wherein the lever drag moves the latch in a proximal direction to allow the latch to contact the ratchet.

19. The apparatus of claim 13, wherein the button lowers a swing pivot to allow the latch to move in a proximal direction to contact the ratchet and prevent the ratchet from engaging the reverse gear.

20. The apparatus of claim 19, wherein a number of staples are ejected in response to the swing pivot being lowered, the button actuated, and the movable handle actuated.

* * * * *